United States Patent
Shimmick (10) Patent No.: US 6,530,916 B1
(45) Date of Patent: *Mar. 11, 2003

(54) UNIFORM LARGE AREA ABLATION SYSTEM AND METHOD

(75) Inventor: John K. Shimmick, Belmont, CA (US)

(73) Assignee: Visx, Incorporated, Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/440,826

(22) Filed: Nov. 15, 1999

(51) Int. Cl.⁷ ............................................. A61B 18/18
(52) U.S. Cl. .............................. 606/5; 606/4; 606/10; 606/11; 128/898
(58) Field of Search .................... 606/4–6, 10, 11, 606/13; 607/88, 89; 128/898

(56) References Cited

U.S. PATENT DOCUMENTS

| | | | |
|---|---|---|---|
| 4,648,400 A | 3/1987 | Schneider et al. | 128/303.1 |
| 4,665,913 A | 5/1987 | L'Esperance, Jr. | 128/303.1 |
| 4,669,466 A | 6/1987 | L'Esperance | 128/303.1 |
| 4,718,418 A | 1/1988 | L'Esperance, Jr. | |
| 4,729,372 A | 3/1988 | L'Esperance, Jr. | 128/303.1 |
| 4,732,148 A | 3/1988 | L'Esperance, Jr. | 128/303.1 |
| 4,770,172 A | 9/1988 | L'Esperance, Jr. | 128/303.1 |
| 4,773,414 A | 9/1988 | L'Esperance, Jr. | 128/303.1 |
| 4,838,266 A * | 6/1989 | Kozio et al. | 128/303.1 |
| 4,856,513 A | 8/1989 | Muller | |
| 4,911,711 A | 3/1990 | Telfair et al. | 606/5 |
| 5,108,388 A | 4/1992 | Trokel | |
| 5,163,934 A | 11/1992 | Munnerlyn | 606/5 |
| 5,207,668 A * | 5/1993 | L'Esperance, Jr. | 606/5 |
| 5,219,344 A | 6/1993 | Yoder, Jr. | 606/5 |
| 5,284,477 A | 2/1994 | Hanna et al. | 606/5 |
| 5,376,086 A * | 12/1994 | Khobehi et al. | 606/4 |
| 5,445,633 A | 8/1995 | Nakamura et al. | 606/5 |
| 5,505,723 A * | 4/1996 | Muller | 606/5 |
| 5,549,599 A | 8/1996 | Sumiya | 606/10 |
| 5,571,107 A | 11/1996 | Shaibani et al. | 606/4 |
| 5,613,965 A | 3/1997 | Muller | 606/5 |
| 5,624,437 A * | 4/1997 | Freeman et al. | 606/12 |
| 5,647,865 A * | 7/1997 | Swinger | 606/5 |
| 5,711,762 A | 1/1998 | Trokel | |
| 5,722,971 A * | 3/1998 | Peyman | 606/5 |
| 5,735,843 A | 4/1998 | Trokel | |
| RE35,974 E | 12/1998 | Davenport et al. | |
| 5,895,384 A * | 4/1999 | Steiner et al. | 606/5 |
| 6,056,739 A * | 5/2000 | Klopotek | 606/5 |

OTHER PUBLICATIONS

John K. Shimmick et al., *Corneal Ablation Profilometry and Steep Central Islands*, J. of Refract. Surg., vol. 13, (May/Jun. 1997), pp. 235–245.

* cited by examiner

Primary Examiner—Linda C. M. Dvorak
Assistant Examiner—A Farah
(74) Attorney, Agent, or Firm—Townsend Townsend & Crew LLP; Mark D. Barrish, Esq.

(57) ABSTRACT

Methods and devices for performing corrective eye surgery generally direct a laser beam at a target region of a patient's eye with the laser beam having a non-uniform energy distribution profile. As ablation rates vary locally across the beam cross-section, the energy distribution profile is tailored to effect a uniform ablation depth with each laser pulse of an excimer laser system.

25 Claims, 6 Drawing Sheets

UNIFORM LARGE AREA ABLATION SYSTEM AND METHOD

BACKGROUND OF THE INVENTION

The present invention relates to methods and systems for performing corrective eye surgery. In particular, the present invention relates to surgical methods and systems providing a laser beam having an energy distribution profile arranged to cause ablation of eye tissue to a generally uniform depth.

Ultraviolet and infrared laser based systems and methods are now used in ophthalmological surgery on the cornea to correct vision defects. These procedures, generally referred to as photorefractive keratectomy, generally employ an ultraviolet or infrared laser to remove a microscopic layer of stromal tissue from the cornea to alter its refractive power. In ultraviolet laser ablation procedures, the radiation ablates corneal tissue in a photodecomposition process that does not cause thermal damage to adjacent and underlying tissue. Molecules at the irradiated surface are broken into smaller volatile fragments without heating the remaining substrate. The mechanism of the ablation is photochemical, i.e., the direct breaking of intermolecular bonds. The ablation removes stromal tissue to change the contour or shape of the cornea for various purposes, such as correcting myopia, hyperopia, and astigmatism. Such systems and methods are disclosed in the following U.S. patents and patent applications, the disclosures of which are hereby incorporated by reference: U.S. Pat. No. 4,665,913 issued May 19, 1987 for "Method for Ophthalmological Surgery"; U.S. Pat. No. 4,669,466 issued Jun. 2, 1987 for "Method and Apparatus for Analysis and Correction of Abnormal Refractive Errors of the Eye"; U.S. Pat. No. 4,732,148 issued Mar. 22, 1988 for "Method for Performing Ophthalmic Laser Surgery"; U.S. Pat. No. 4,770,172 issued Sep. 13, 1988 for "Method of Laser-Sculpture of the Optically Used Portion of the Cornea"; U.S. Pat. No. 4,773,414 issued Sep. 27, 1988 for "Method of Laser-Sculpture of the Optically Used Portion of the Cornea"; U.S. patent application Ser. No. 07/109,812 filed Oct. 16, 1987 for "Laser Surgery Method and Apparatus" now U.S. Pat. Nos. 5,108,388; 5,163,934 issued Nov. 17, 1992 for "Photorefractive Keratectomy"; U.S. patent application Ser. No. 08/368,799, filed Jan. 4, 1995 for "Method and Apparatus for Temporal and Spatial Beam Integration" now U.S. Pat. No. 5,646,791; U.S. patent application Ser. No. 08/138,552, filed Oct. 15, 1993 for "Method and Apparatus for Combined Cylindrical and Spherical Eye Corrections" now U.S. Pat. No. 5,713,892; U.S. patent application Ser. No. 08/058,599, filed May 7, 1993 for "Method and System for Laser Treatment of Refractive Errors Using Offset Imaging" now abandoned; and U.S. patent application Ser. No. 09/303,810, filed Apr. 30, 1999 for "Method and System for Ablating Surfaces with Partially Overlapping Craters Having Consistent Curvature".

Refractive surgery often makes use of laser ablation to selectively remove corneal tissues, thereby resculpting the cornea to reduce myopia, hyperopia, astigmatism, or other refractive defects. This resculpting generally directs varying amounts of laser energy across the cornea. The lasers often produce beams comprising a series of laser pulses, and the laser systems generally vary a size, shape, and/or location of these pulses to effect the predetermined resculpting.

Figure 1:
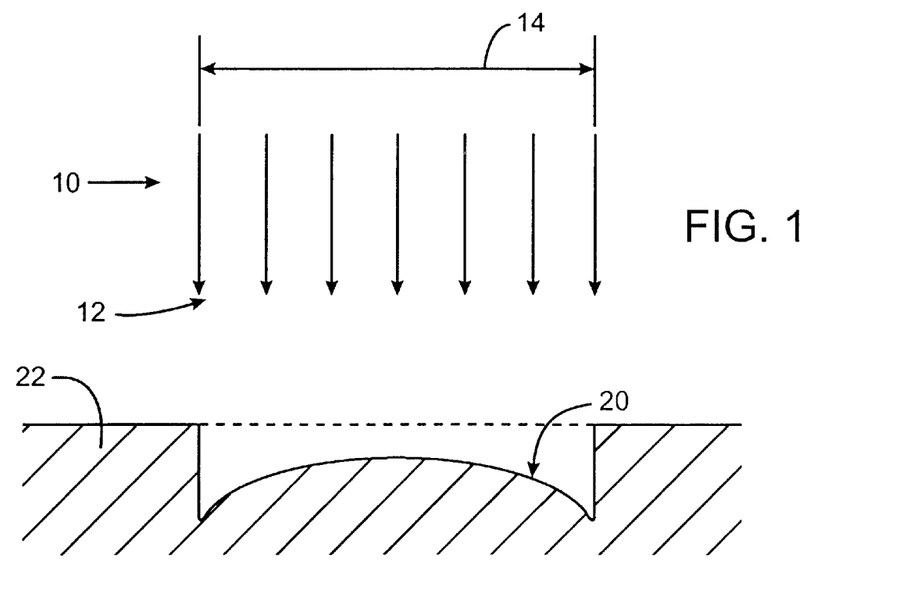
FIG. 1 shows a schematic side view of a laser beam having a uniform energy distribution profile extending across its cross-sectional area and a resultant ablation area of non-uniform depth on an eye of a patient.

The lasers used in laser eye surgery systems often produce beams having Gaussian energy distribution profiles, as measured across a cross-section of the laser beam. These systems often include optical elements (sometimes referred to as integrators) which modify the energy distribution to a more uniform profile. Unfortunately, work in connection with the present invention has found that when a laser beam having a uniform energy distribution profile extending across its cross-sectional area is used to remove or to sculpt eye tissue, a non-uniform ablation depth ensues. Referring to FIG. 1 of the accompanying drawings a laser beam having a uniform energy distribution profile is indicated at 10, the resultant non-uniform ablation depth being indicated at 20. This non-uniform ablation depth reduces the overall accuracy of the resculpting procedure, thereby limiting the benefits of these new systems.

In light of the above, it would be desirable to provide improved devices, systems, and methods for laser eye surgery. It would further be desirable if these improvements did not increase the complexity and cost of the laser system, and made use of laser ablation algorithms or treatment protocols which reflected actual experience in ablations, rather than relying on simplified theoretical ablation depth calculations. It would further be advantageous if these improvements did not prolong the total treatment time and reduced the number of individual ablations which are used to effect a desired resculpting so as to avoid additional ablation edge-induced surface roughness.

SUMMARY OF THE INVENTION

According to one aspect of the invention, there is provided a method of performing corrective eye surgery, the method comprising directing a laser beam at a cornea region of an eye of a patient, the laser beam having a cross-sectional area; and adapting an energy distribution profile extending across the cross-sectional area of the laser beam to provide a resultant laser beam having a non-uniform energy distribution profile so as to cause a generally uniform ablation depth when the cross-sectional area of the laser beam is directed at the cornea region of the patient's eye.

The adapting step can comprise causing the laser beam to have a centrally disposed higher energy region surrounded by a peripheral lower energy region.

The method can further comprise generating the laser beam with a generally Gaussian energy distribution profile extending across its cross-sectional area, the adapting step changing the Gaussian profile to provide the resultant energy distribution profile.

The adapting step can comprise directing the laser beam through a diffractive optic.

The cross-sectional area of the laser beam can be circular in shape.

The method can comprise passing the laser beam through a generally rotationally symmetrical aperture.

The generally rotationally symmetrical aperture can be defined by an iris diaphragm imaged at a distance removed from the corneal region so as to form an out-of-focus image of the iris on the corneal region.

Instead, the generally rotationally symmetrical aperture can be defined by an iris diaphragm imaged on the corneal region, the method including rotating the imaged iris diaphragm.

The laser beam can comprise a series of pulses at a given location, the method comprising angularly displacing the iris diaphragm between the laser beam pulses.

The cross-sectional area of the resultant laser beam can correspond with an area of an epithelial layer extending across an entire surgical site of the eye so as to cause uniform ablation of the epithelial layer across the entire surgical site.

The method can include using the resultant laser beam to uniformly ablate the epithelial layer across the entire surgical site, and then selectively masking portions of the cross-sectional area of the laser beam to sculpt at least part of a stroma surface of the eye to a required shape, after the epithelial layer is uniformly ablated.

According to another aspect of the invention, there is provided a corrective eye surgery system including a laser for generating a laser beam having a cross-sectional area and an energy distribution profile extending across the cross-sectional area; and an optical element disposed in the laser beam and adapting the energy distribution profile of the laser beam to provide a resultant laser beam having a non-uniform resultant energy distribution profile producing a generally uniform ablation depth when the cross-sectional area of the laser beam is directed at a cornea region of a patient's eye.

The resultant energy distribution can have a centrally disposed higher energy region surrounded by a peripheral lower energy region.

The laser beam can have a generally Gaussian energy distribution profile extending across its cross-sectional area.

The optical element can comprise a diffractive optic through which the laser beam is passed to yield the resultant laser beam.

The cross-sectional area of the resultant laser beam can be circular in shape.

The corrective eye surgery system can further include an arrangement defining a generally rotationally symmetrical aperture.

The corrective eye surgery system can further comprise an imaging system directing an out-of-focus iris image onto the patient's eye.

The rotationally symmetrical aperture can be defined by an imaged iris, the system further including a drive arrangement associated with the imaged iris for causing angular displacement of the imaged iris about an axis of the laser beam.

The cross-sectional area of the resultant laser beam can correspond to an area of an epithelial layer extending across an entire surgical site of the eye to cause uniform ablation of the epithelial layer across the entire surgical site.

The corrective eye surgery system can further include a masking arrangement for selectively masking portions of the laser beam to sculpt a stroma surface after the epithelial layer has been uniformly ablated.

BRIEF DESCRIPTION OF THE DRAWINGS

The invention will now be described, by way of example, and with reference to the accompanying drawings, in which.

DESCRIPTION OF THE SPECIFIC EMBODIMENTS

Referring to FIG. 1 of the drawings, a laser beam having a uniform energy distribution profile, schematically indicated by reference numeral 12, extending across its cross-sectional area 14 is generally indicated by reference numeral 10. The laser beam 10 is being used to ablate a patient's eye during a corrective eye surgical procedure. Part of an eye surface of the patient's eye is indicated by reference numeral 22. The cross-sectional area 14 of the laser beam 10 is typically circular. It has been found that when such a laser beam 10 is used in the course of the corrective surgical procedure, an ablation area of non-uniform depth is formed. Reference numeral 20 indicates a typical ablation area of non-uniform depth formed on the patient's eye by the laser 10. In particular, the depth of the ablation 20 is at its shallowest at a central region and is at its deepest at a peripheral region surrounding the central region. It will be appreciated that the non-uniform depth of the ablation has been exaggerated in FIG. 1 for illustrative purposes.

Figure 2:
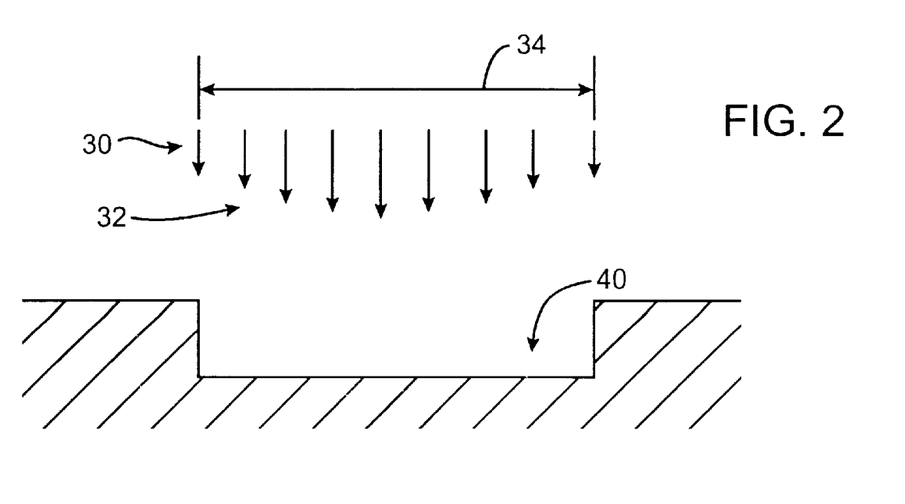
FIG. 2 shows a schematic side view of a laser beam in accordance with the invention having a non-uniform energy distribution profile extending across its cross-sectional area and a resultant ablation area of uniform depth on an eye of a patient.

Referring now to FIG. 2 of the drawings, a laser beam in accordance with the invention is generally indicated by reference numeral 30. The laser beam 30 has a non-uniform energy distribution profile, schematically indicated at 32, extending across its cross-sectional area 34. The cross-sectional area 34 of the laser beam 30 is typically circular. The energy distribution across the cross-sectional area 34 is higher at a centrally disposed region and is lower at a surrounding peripheral region. The energy distribution profile of the laser beam 30 is arranged to produce an ablation on the eye tissue of a uniform depth, as indicated by reference numeral 40, during the course of a surgical eye procedure.

Figure 3:
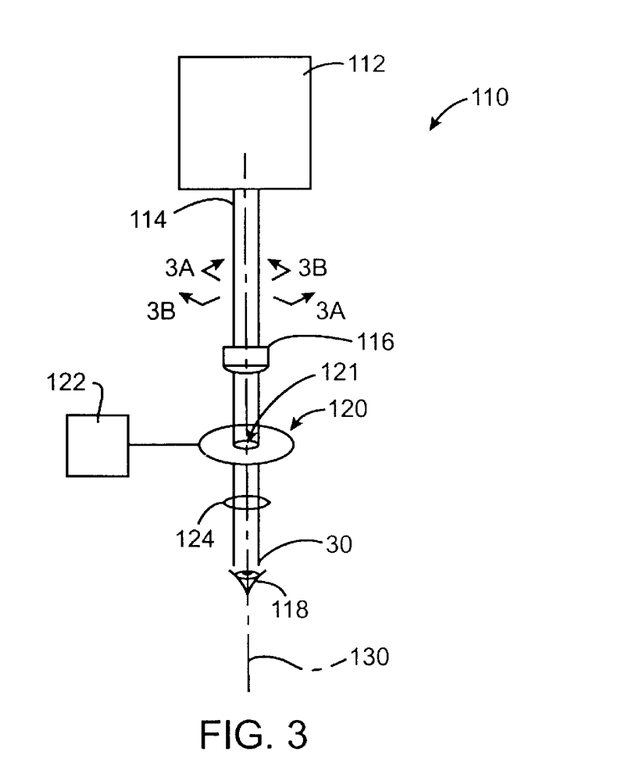
FIG. 3 shows a schematic diagram indicating a corrective eye surgery system in accordance with the invention.

Referring to FIG. 3 of the drawings, a corrective eye surgery system in accordance with the invention is generally indicated by reference numeral 110. The system 110 is arranged to produce the laser beam 30.

Figure 3A:
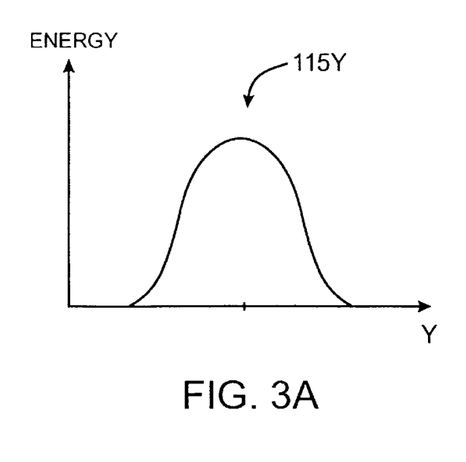
FIGS. 3A and 3B schematically illustrate energy distribution profiles for perpendicular cross-sections of a laser beam as generated by a laser.
Figure 3B:
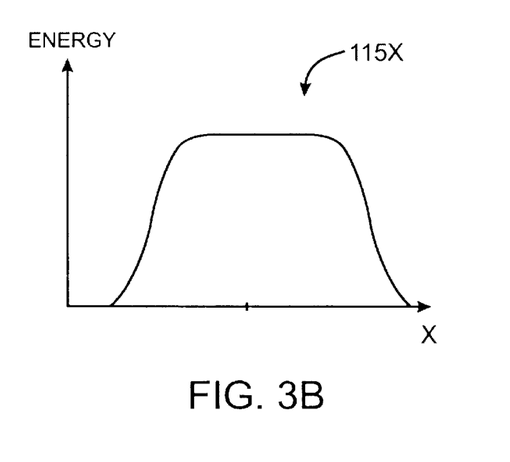

The system 110 includes a laser beam generating source 112. The source 112 typically generates a laser beam as indicated at 114 which typically has a Gaussian energy distribution profile 115 extending across a first cross-section of the beam 3A—3A as shown in FIG. 3A. A second cross-section 3B—3B of the laser beam 114 will typically have a more uniform energy distribution profile 115x, as shown in FIG. 3B.

Suitable ablative laser beam sources include excimer, free electron and solid state lasers emitting ultraviolet light and pulsed infrared lasers. A suitable energy source emits energy that is strongly absorbed by the tissue so that most of the energy is absorbed within about a 1 um depth into the tissue.

An example of a suitable excimer laser is an argon fluoride excimer laser emitting ultraviolet light having a wavelength of 193 nm. An example of a suitable solid state laser is a laser producing an ultraviolet light energy having a wavelength of 213 nm that is generated by a fifth harmonic from a yttrium aluminum garnet (YAG) laser having a fundamental wavelength of 1064 nm. An example of a suitable infrared laser is a erbium YAG laser producing light energy having a wavelength of 2.9 microns. The following patents describe suitable ablative energy sources and the fall disclosures of these patents are herein incorporated by reference: U.S. Pat. No. 5,782,822 (by Telfair) and U.S. Pat. No. 5,520,679 (by Lin).

The system 110 further includes an adapter arrangement generally indicated at 116. The adapter arrangement 116 adapts the Gaussian energy distribution profile extending across the cross-sectional area of the laser beam 114 to provide a resultant laser beam which is the laser beam 30 and which has a non-uniform energy distribution profile arranged to cause a generally uniform ablation depth when the cross-sectional area of the resultant laser beam 30 is used to ablate typically a cornea region of the patient's eye indicated at 118.

As mentioned with reference to FIG. 2 of the drawings, the laser beam 30 is adapted to have an energy distribution profile extending across its cross-sectional area which has a centrally disposed higher energy density region surrounded by a peripheral lower energy density region. The adapter arrangement 116 is typically in the form of an optical element. Where the laser beam 114 has a Gaussian energy distribution, the optical element is typically in the form of a diffractive optic which adapts the Gaussian energy distribution profile to decrease its centrally disposed energy density and to increase its peripheral energy density.

Figure 3C:
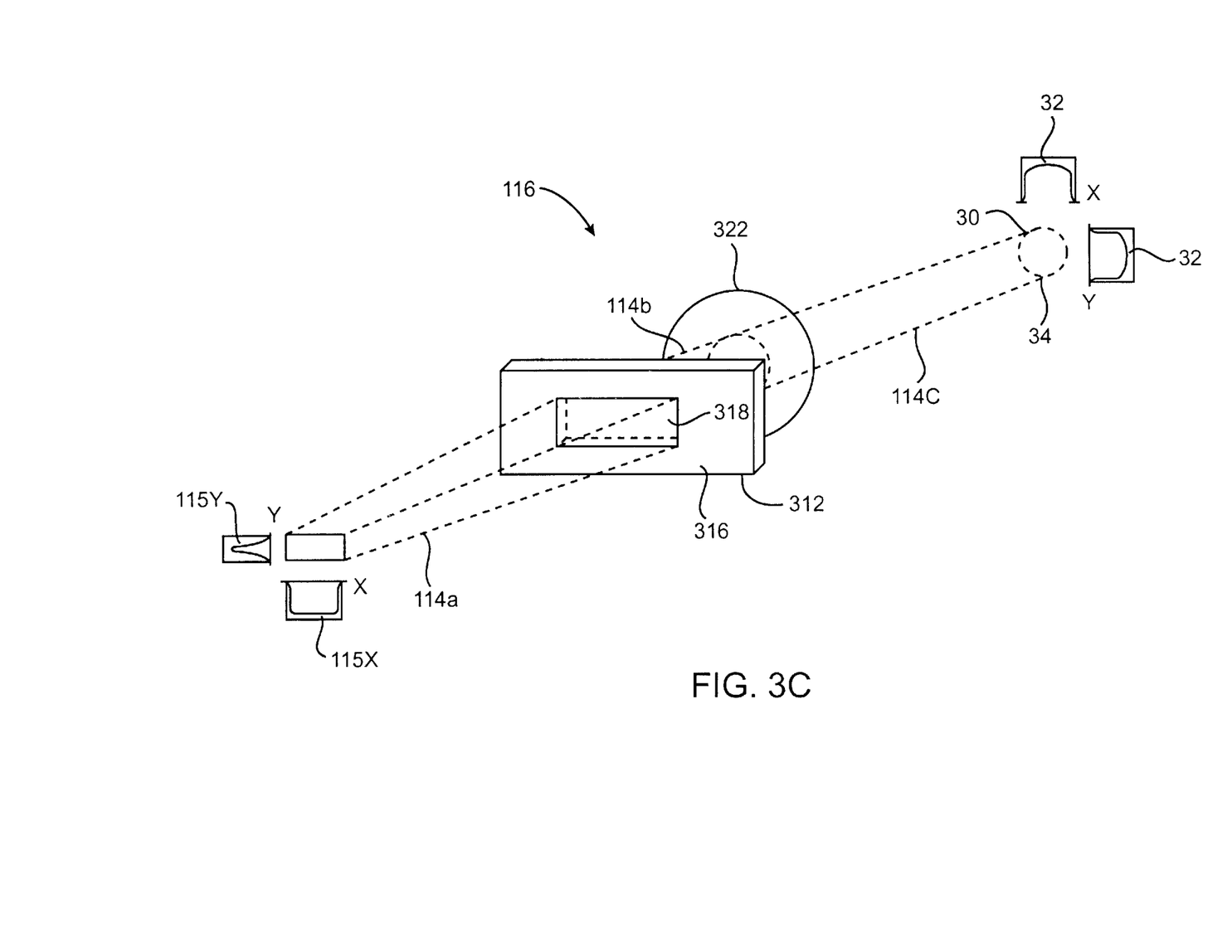
FIG. 3C illustrates a beam energy adapter arrangement including a diffractive optic and a lens.

An exemplary adapter arrangement 116 is illustrated in more detail in FIG. 3C. Laser beam 114 often initially comprises a substantially rectangular cross-section beam 114a. As described above, the intensity along a first cross-section of beam 114a is generally uniform, while the intensity along the shorter perpendicular cross-section is substantially Gaussian. Beam 114a is directed toward a diffractive element 312 having a generally planer body 316 that includes a transparent portion 318, the transparent portion receiving and diffractively transforming the laser beam. The diffracted beam 114b immerging from diffractive element 312 travels along the beam axis through a positive or converging lens 322 which converges the diffracted beam. The converged beam again 114c continues along the beam axis to produce the desired energy distribution 32 and cross-sectional area 34.

In the exemplary embodiment, transparent portion 318 has a generally rectangular shape sized for receiving the entire rectangular beam 114a. For beams which are not rectangular, transparent portion 318 may alternatively be circular, square, or other appropriate shapes. Transparent portion 318 of diffractive element 312 has a diffractive pattern etched in a transparent medium. The transparent medium may be a glass-like silica material. The transparent medium desirably is substantially non-absorbent and non-reflective to beam 114. Exemplary transparent mediums include fused silica, quartz, magnesium fluoride, calcium fluoride, lithium fluoride, sapphire, or the like.

The diffractive pattern on transparent medium 318 is configured to transform the Gaussian laser beam to an adapted energy distribution which remains non-uniform across the cross-sectional area of the beam, but which ablates a uniform ablation depth from corneal tissue. Calculation of the desired energy distribution may be performed by measuring ablation depths across an ablation as effected by a uniform energy distribution, and locally adjusting the energy distribution according to the local ablation rates so as to provide a uniform ablation depth.

The cross-sectional shape of the converged beam 114c may be circular, rectangular, or the like. For laser eye surgery, a circular cross-sectional area is often desirable.

The configuration of the diffractive pattern may depend largely on the shape, spatial intensity distribution, and wavelength of beam 114a generated by the laser. The diffractive pattern may include a plurality of properly spaced etched regions such as lines, spots, or the like. For excimer lasers with short wavelengths in the neighborhood of about 193 nanometers, the spacings of the etched regions in the diffractive pattern are preferably small and precise, and may be formed using known etching techniques such as dry etching of the material of transparent portion 118.

Exemplary related diffractive optic elements for spatial and/or temporal integration so as to provide a uniform energy distribution are more fully described in copending U.S. patent application Ser. No. 09/015,841, filed on Jan. 29, 1998 (the full disclosure of which is incorporated herein by reference). Alternative beam energy adapting elements 116 may comprise systems including lenses, prisms, energy absorbing materials including polymers, fluids, or gels, and the like. An exemplary binary optic for spatial integration so as to provide a substantially uniform energy distribution was designed by Digital Optics Corporation of Charlotte, N.C., although other companies skilled in the art of diffractive optic design can produce similar gratings. Such gratings may be modified to produce the uniform ablation depth of the present invention by, for example, varying a separation among converging lens 322, diffractive element 312, and a spatial integration plane, by varying the diffractive pattern on the diffractive element 312, or the like. Alternative beam energy adaptor arrangements providing the desired energy distribution profile may also be similar to the structures more fully described in copending U.S. patent application Ser. No. 09/303,810, filed Apr. 30, 1999, the full disclosure of which is incorporated herein by reference. Still further alternative beam energy distribution adapting elements may have structures similar to those described in U.S. Pat. No. 5,610,733, the full disclosure of which is also incorporated herein by reference.

The system 110 further includes an arrangement 120 defining a rotationally symmetrical aperture at 121. The rotationally symmetrical aperture 121 can be defined by an imaged iris. A drive arrangement 122 associated with the imaged iris is then provided to drive the imaged iris to displace about an axis 130 of the laser treatment. The drive arrangement 122 is arranged to drive the imaged iris to displace in a sequential manner between pulses of the laser beam 30, thereby to inhibit asymmetric irregularities from forming during the surgical procedure on the eye. System 110 may further include an imaging lens 124 for forming an image of aperture 121 near eye 118.

Instead, the rotationally symmetrical aperture 121 can be defined by an imaging system directing an out-of-focus iris image onto the patient's eyes. In one application, the corrective eye surgery system 110 can advantageously be used uniformly to ablate an area of an epithelial layer extending across an entire surgical site of the patient's eye.

Figure 4:
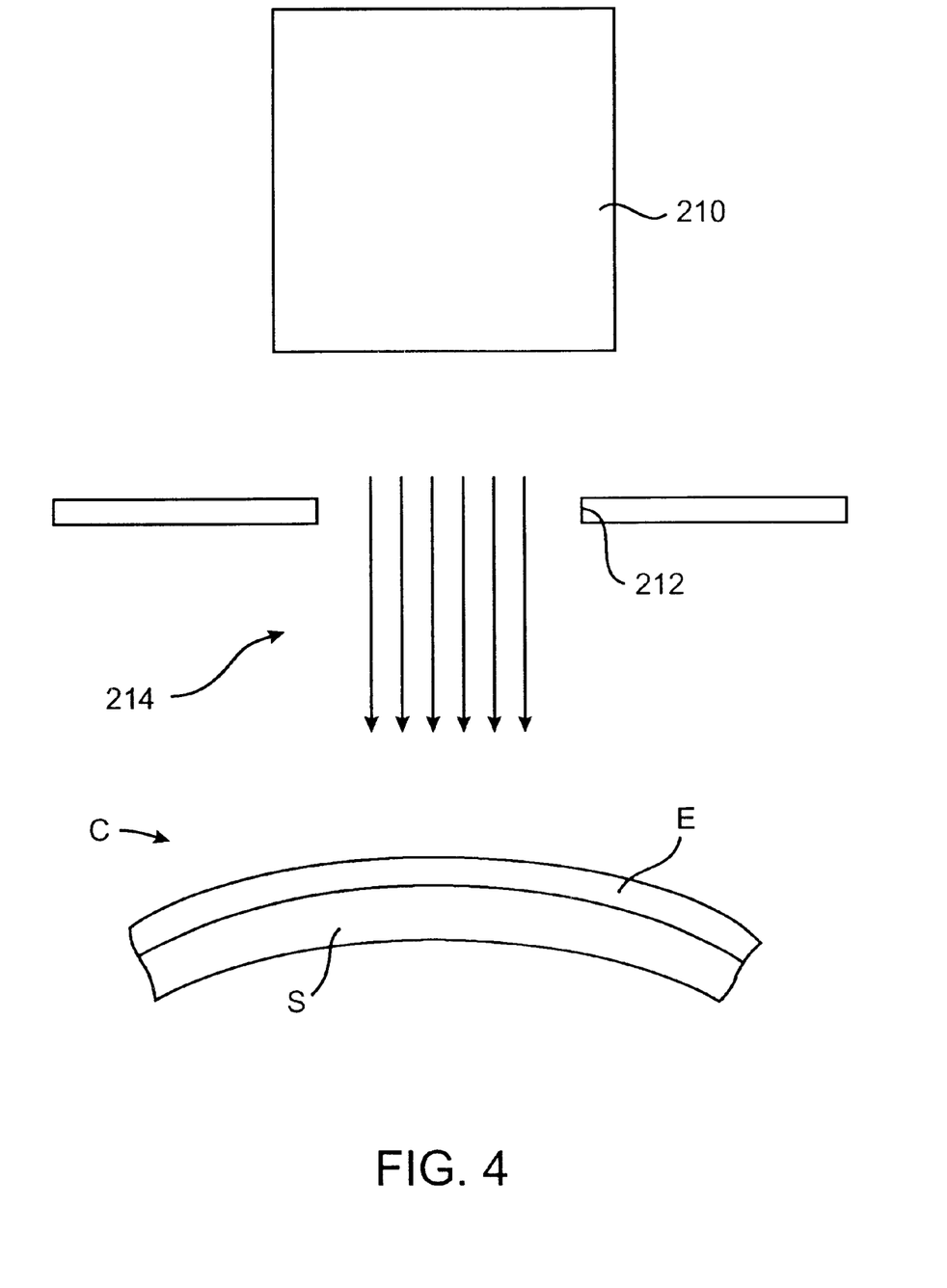
FIG. 4 shows a schematic side view of a laser beam having a uniform energy distribution profile extending across its cross-sectional area, the laser beam being used to ablate an area of an epithelial layer extending across an entire surgical site.
Figure 5:
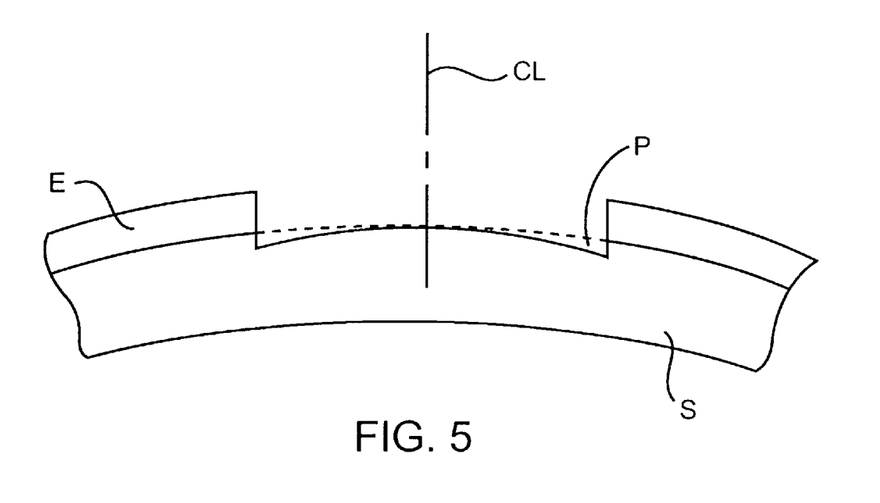
FIG. 5 shows a schematic side view of a resultant ablation after the epithelial layer is ablated by the laser beam of FIG. 4.
Figure 6:
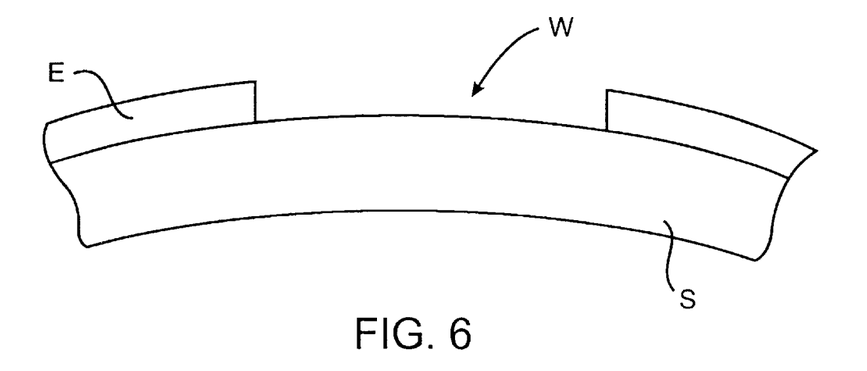
FIG. 6 shows a schematic side view of the resultant ablation of FIG. 5 after correction of initial excess removal has been effected.

When a laser beam of uniform energy distribution extending across its cross-sectional area is used for ablation of an exposed area extending across a surgical site, excessive removal of peripheral portions, typically resulting in excessive removal of stromal tissue, often ensues. Referring to FIGS. 4 to 6 of the drawings, when a laser beam generated at 210 is passed through an aperture 212 so that a single beam of ablative radiation 214 is directed at the epithelial layer E disposed over the stromal layer S in the cornea C, it has been found that exposure of the epithelial layer E for a time sufficient to remove the full thickness of the layer at a center line CL results in excess removal of corneal material in the peripheral region P, as illustrated in FIG. 5. As can be seen, the epithelial layer E has been completely removed in the peripheral region P. In addition, a portion of the stromal layer S in peripheral region P has also been removed. Such reshaping of the exposed stromal surface prior to corrective treatment can adversely affect the subsequent treatment. While the initial, unintended reshaping of the stromal surface can be offset, for example, in the case of myopia, by increasing the diopter (flattening) of the subsequent laser treatment, the combined initial removal of the stromal material and subsequent correction of the initial removal results in a depression or well W being formed in the stromal layer, as illustrated in FIG. 6. While such an outcome has not been found to be clinically significant, it is undesirable to remove more stromal material than the amount which is necessary to effect the desired corneal reshaping.

By means of the laser beam 30 of the invention, the epithelial layer can be removed more uniformly. This is achieved, as herein before described, by adapting the energy distribution profile across the cross-sectional area of the laser beam to provide a resultant laser beam which, when directed across an area of the epithelial layer extending across the entire surgical site, ablates the epithelial layer uniformly so that the stroma is revealed without excessive peripheral removal of stromal tissue.

After the epithelial layer is thus removed, the same laser beam can be used to sculpt the stromal layer by selectively masking portions of the laser beam 30 in accordance with known methods. This can typically be achieved by selectively masking annular peripheral regions of the beam so as to produce a beam of varying diameter. It should be noted that the enhanced energy central region of the laser beam may lead to overall ablation depths increasing in a controlled manner with decreasing diameter. This can typically be compensated for during, for example, photorefractive keratectomy ablation by use of an ablation pulse directing algorithm of the system 110 which provides relatively fewer laser beam pulses at smaller ablation diameters. In such a case, the system 110 is typically controlled through a processor, the algorithm being programmed into the processor to yield a suitable operating relationship between the number of laser beam pulses and the diameter of the beam directed at the eye to effect a given ablation depth.

Figure 7:
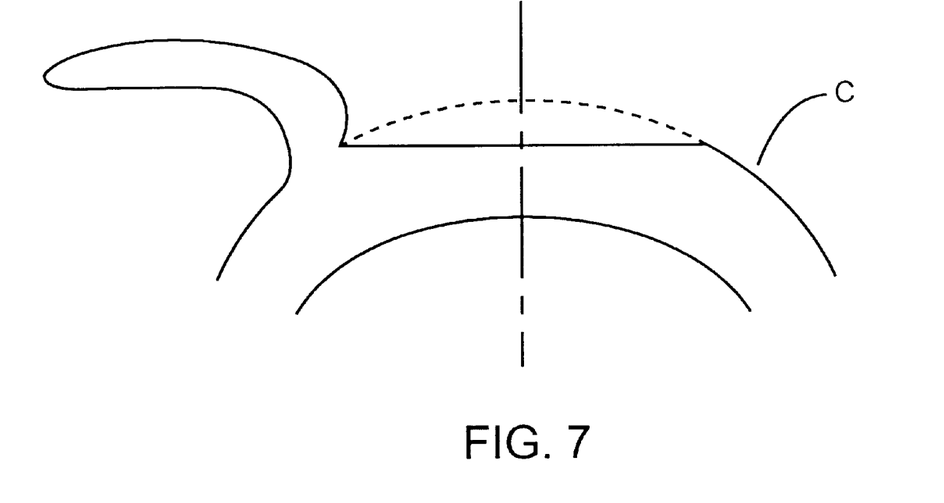
FIGS. 7 and 8 schematically illustrate a method for forming a uniform ablation using a non-uniform laser beam in a LASIK resculpting procedure, according to the principles of the present invention.
Figure 8:
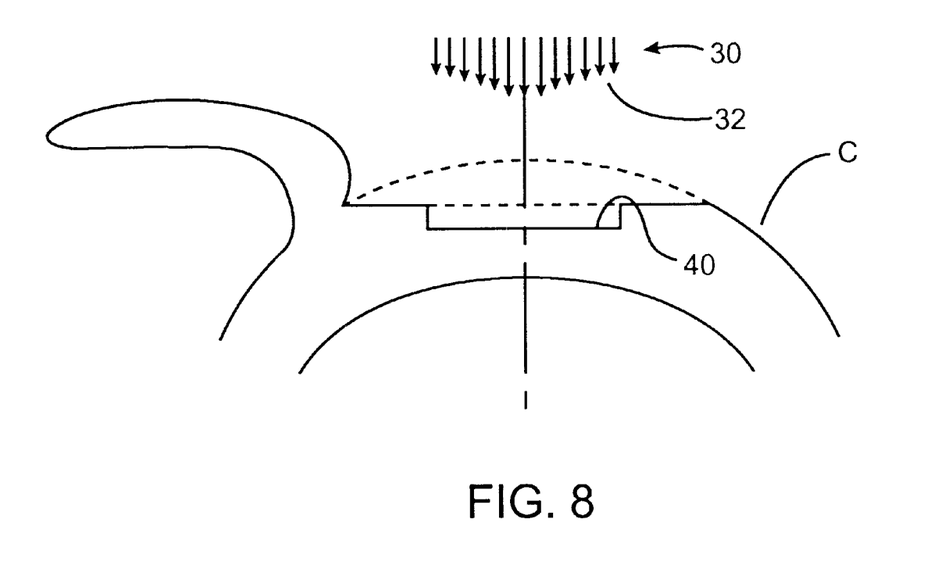

The uniform ablation depth provided by a non-uniform laser beam may enhance a variety of laser eye therapies, including laser in situ keratomileusis (LASIK), photorefractive keratectomy (PRK), phototherapeutic keratectomy (PTK), and the like. A LASIK procedure is schematically illustrated in FIGS. 7 and 8, and generally involves incising Cornea C with a microkeratome and displacing a flap F of the corneal tissue to expose the stroma. As described above, a laser beam 30 (often comprising one or more pulses) with a non-uniform energy distribution 32 forms a uniform-depth ablation 40 in the stromal tissue across the cross-sectional area of the laser beam. By varying the size, shape, and/or location of beam 30 upon the exposed stromal surface, flexible resculpting of the cornea can be effected. When flap F is repositioned, the flap reattaches to the treated surface, so that the combined total ablations will alter the refractive characteristics of the healed eye to improve vision.

Although the invention has been described with specific reference to uniform ablation across the entire surgical site, it is to be appreciated that the same principles of adapting the laser beam to have a non-uniform energy profile corresponding to ablation to a uniform depth can typically be used in a resculpting procedure involving sequentially scanning the laser beam across the surgical site. In such a case, localized portions of the surgical site are treated in accordance with a predetermined sequence so as to resculpt the entire site. Thus, adapting the laser beam to have a non-uniform energy distribution profile corresponding to a uniform ablation depth, can also be applied to laser beam diameters corresponding to only portions of the surgical site.

While this invention has been particularly shown and described with references to preferred embodiments thereof, it will be understood by those skilled in the art that various changes in form and details may be made thereto without departing from the spirit and scope of the invention as defined in the accompanying claims.

What is claimed is:

1. A method of performing corrective eye surgery, the method comprising:

directing a laser beam at a cornea region of an eye of a patient, the laser beam having a cross-sectional area and an energy distribution profile extending across the cross-sectional area of the laser beam;

determining a desired non-uniform energy distribution profile, the desired non-uniform profile having a central region with a first energy intensity and a peripheral region with a second energy intensity, the desired non-uniform profile being determined such that the second energy intensity is sufficiently lower than the first energy intensity to compensate for a local peripheral ablation rate being higher than a local central ablation rate so as to produce a generally uniform ablation rate depth across the laser beam;

adapting the energy distribution profile extending across the cross-sectional area of the laser beam to provide a resultant laser beam having the desired non-uniform energy distribution profile adjacent the eye wherein the adapting step comprises directing the laser beam through a diffractive optic; and ablating corneal tissue of the eye with the resultant laser beam so that the non-uniform energy profile effects a generally uniform ablation depth across the cross-sectional area of the beam.

2. A method of performing corrective eye surgery as claimed in claim 1, further comprising generating the laser beam with a generally Gaussian energy distribution profile extending across its cross-sectional area, the adapting step changing the Gaussian profile to provide the resultant energy distribution profile.

3. A method of performing corrective eye surgery as claimed in claim 1, wherein the cross-sectional area of the laser beam is circular in shape.

4. A method of performing corrective eye surgery as claimed in claim 1, further comprising passing the laser beam through a generally rotationally symmetrical aperture.

5. A method of performing corrective eye surgery as claimed in claim 4, wherein the generally rotationally symmetrical aperture is defined by an iris diaphragm imaged at a distance removed from the corneal region so as to form an out-of-focus image of the iris diaphragm on the corneal region.

6. A method of performing corrective eye surgery as claimed in claim 4, wherein the generally rotationally symmetrical aperture is defined by an iris diaphragm imaged on the corneal region, the method including rotating the imaged iris diaphragm.

7. A method of performing corrective eye surgery as claimed in claim 6, wherein the laser beam comprises a series of pulses at a given location, the method comprising angularly displacing the iris diaphragm between the laser beam pulses.

8. A method of performing corrective eye surgery as claimed in claim 1, wherein the cross-sectional area of the resultant laser beam corresponds with an area of an epithelial layer extending across an entire treatment target site of the eye so as to cause uniform ablation of the epithelial layer across the entire site.

9. A method of performing corrective eye surgery as claimed in claim 8, including using the resultant laser beam uniformly to ablate the epithelial layer across the entire treatment target site, and then selectively masking portions of the cross-sectional area of the laser beam to sculpt at least part of a stroma surface of the eye to a required shape, after the epithelial layer is uniformly ablated.

10. A corrective eye surgery system including a laser for generating a laser beam having a cross-sectional area and an energy distribution profile extending across the cross-sectional area; and an optical element disposed in the laser beam, the optical element comprising a diffractive optic, the diffractive optic configured so as to adapt the energy distribution profile of the laser beam to provide a resultant laser beam having a non-uniform resultant energy distribution profile adjacent a target location, the non-uniform profile comprising a central region having a first energy intensity and a peripheral region having a second energy intensity, the second energy intensity sufficiently lower than the first energy intensity to compensate for peripheral overablation induced by uniform ablation energy such that the non-uniform profile produces a generally uniform ablation depth across the cross-sectional area of the non-uniform laser beam when the resultant laser beam is directed at a cornea region of a patient's eye disposed at the target location.

11. A corrective eye surgery system as claimed in claim 10, wherein the laser beam has a generally Gaussian energy distribution profile extending across its cross-sectional area.

12. A corrective eye surgery system as claimed in claim 10, wherein the cross-sectional area of the resultant laser beam is circular in shape.

13. A corrective eye surgery system as claimed in claim 10, which further includes an arrangement defining a generally rotationally symmetrical aperture.

14. A corrective eye surgery system as claimed in claim 13, further comprising an imaging system directing an out-of-focus iris image onto the patient's eye.

15. A corrective eye surgery system as claimed in claim 13, wherein the rotationally symmetrical aperture is defined by an imaged iris and the system further includes a drive arrangement associated with the imaged iris for causing angular displacement of the imaged iris about an axis of the laser beam.

16. A corrective eye surgery system as claimed in claim 10, wherein the cross-sectional area of the resultant laser beam corresponds to an area of an epithelial layer extending across an entire surgical site of the eye to cause uniform ablation of the epithelial layer across the entire surgical site.

17. A corrective eye surgery system as claimed in claim 16, which further includes a masking arrangement for selectively masking portions of the laser beam to sculpt a stroma surface after the epithelial layer has been uniformly ablated.

18. A corrective eye surgery system comprising:

a laser for generating a laser beam, the laser beam comprising a series of laser pulses, the pulses having cross-sectional areas and energy distribution profiles extending across the cross-sectional areas; and an optical element disposed in the laser beam, the optical element including a diffractive optic through which the laser beam passes, the diffractive optic adapting the energy distribution profile of each laser beam pulse to provide a resultant laser beam pulse having non-uniform resultant energy distribution profile, the non-uniform profiles comprising central regions having first energy intensities and peripheral regions having second energy intensities, the diffractive optic causing the second energy intensities to be sufficiently lower than the first energy intensities to compensate for peripheral overablation induced by uniform energy and produce a generally uniform ablation depth when each pulse of the resultant non-uniform laser beam is directed at a cornea region of a patient's eye.

19. A corrective eye surgery system as claimed in claim 18, wherein the laser beam has a generally Gaussian energy distribution profile extending across its cross-sectional area.

20. A corrective eye surgery system as claimed in claim 18, wherein the cross-sectional area of the resultant laser beam is circular in shape.

21. A corrective eye surgery system as claimed in claim 18, which further includes an arrangement defining a generally rotationally symmetrical aperture.

22. A corrective eye surgery system as claimed in claim 21, further comprising an imaging system directing an out-of-focus iris diaphragm image onto the patient's eye.

23. A corrective eye surgery system as claimed in claim 21, wherein the rotationally symmetrical aperture is defined by an imaged iris diaphragm and the system further includes a drive arrangement associated with the imaged iris diaphragm for causing angular displacement of the imaged iris diaphragm about an axis of the laser beam.

24. A corrective eye surgery system as claimed in claim 18, wherein the cross-sectional area of the resultant laser beam corresponds to an area of an epithelial layer extending across an entire surgical site of the eye to cause uniform ablation of the epithelial layer across the entire surgical site.

25. A corrective eye surgery system as claimed in claim 24, which further includes a masking arrangement for selectively masking portions of the laser beam to sculpt a stroma surface after the epithelial layer has been uniformly ablated.

* * * * *